United States Patent
Flexman et al.

(10) Patent No.: US 10,350,011 B2
(45) Date of Patent: Jul. 16, 2019

(54) LUMEN DESIGN FOR OPTIMAL FIBER INTEGRATION FOR OPTICAL SHAPE SENSING

(71) Applicant: KONINKLIJKE PHILIPS N.V., Eindhoven (NL)

(72) Inventors: Molly Lara Flexman, New York, NY (US); David Paul Noonan, New York, NY (US); Raymond Chan, San Diego, CA (US); Franciscus Reinier Antonius Van Der Linde, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 677 days.

(21) Appl. No.: 14/423,535

(22) PCT Filed: Sep. 24, 2013

(86) PCT No.: PCT/IB2013/058806
§ 371 (c)(1),
(2) Date: Feb. 24, 2015

(87) PCT Pub. No.: WO2014/049519
PCT Pub. Date: Apr. 3, 2014

(65) Prior Publication Data
US 2015/0209117 A1    Jul. 30, 2015

Related U.S. Application Data

(60) Provisional application No. 61/706,822, filed on Sep. 28, 2012.

(51) Int. Cl.
*A61B 34/20* (2016.01)
*A61B 17/00* (2006.01)
*A61B 90/00* (2016.01)

(52) U.S. Cl.
CPC ...... *A61B 34/20* (2016.02); *A61B 2017/0084* (2013.01); *A61B 2017/00876* (2013.01); *A61B 2017/00929* (2013.01); *A61B 2034/2046* (2016.02); *A61B 2034/2061* (2016.02); *A61B 2090/373* (2016.02); *A61B 2562/12* (2013.01)

(58) Field of Classification Search
None
See application file for complete search history.

(56) References Cited

U.S. PATENT DOCUMENTS

| 6,206,824 B1 | 3/2001 | Ohara et al. |
| 6,471,710 B1 | 10/2002 | Bucholtz |
| 7,117,703 B2 | 10/2006 | Kato et al. |
| 8,050,523 B2 | 11/2011 | Younge et al. |

(Continued)

FOREIGN PATENT DOCUMENTS

| JP | H0591972 A | 4/1993 |
| JP | H06154156 A | 6/1994 |

*Primary Examiner* — Katherine L Fernandez

(57) ABSTRACT

A shape sensing enabled instrument includes a flexible longitudinal body (300) including a plurality of longitudinal members (310) held together to form a lumen (205). The longitudinal members have frictional contact therebetween and are configured to engage neighboring longitudinal members during bending, twisting or external pressure to maintain dimensions of the lumen. A shape sensing optical fiber (302) is disposed within the lumen.

16 Claims, 4 Drawing Sheets

(56) References Cited

U.S. PATENT DOCUMENTS

| | | |
|---|---|---|
| 2004/0098028 A1* | 5/2004 | Martinez .......... A61B 17/12022 |
| | | 606/200 |
| 2004/0111010 A1 | 6/2004 | Nishiie |
| 2006/0014418 A1 | 1/2006 | Kato et al. |
| 2007/0116408 A1* | 5/2007 | Eberle ................ A61B 1/00165 |
| | | 385/31 |
| 2009/0123111 A1* | 5/2009 | Udd ........................ A61B 5/06 |
| | | 385/13 |
| 2011/0087070 A1* | 4/2011 | Tilson ................ A61B 1/00135 |
| | | 600/121 |
| 2011/0319910 A1* | 12/2011 | Roelle ................... A61B 34/71 |
| | | 606/130 |
| 2013/0165945 A9 | 6/2013 | Roelle et al. |
| 2015/0209117 A1 | 7/2015 | Flexman et al. |

* cited by examiner

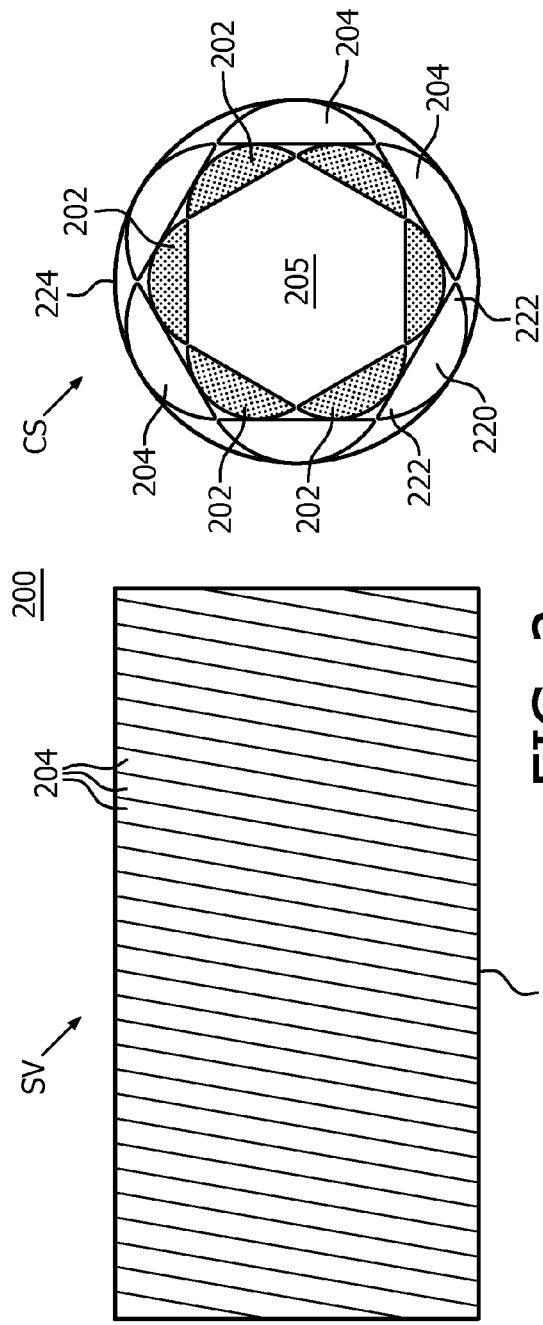
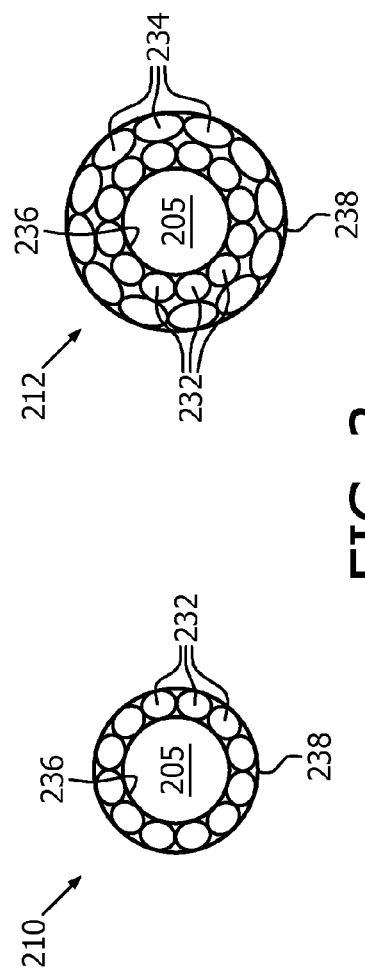
FIG. 2
FIG. 3

LUMEN DESIGN FOR OPTIMAL FIBER INTEGRATION FOR OPTICAL SHAPE SENSING

CROSS-REFERENCE TO PRIOR APPLICATIONS

This application is the U.S. National Phase application under 35 U.S.C. § 371 of International Application Serial No. PCT/IB2013/058806, filed on Sep. 24, 2013, which claims the benefit of U.S. Application Ser. No. 61/706,822, filed on Sep. 28, 2012. These applications are hereby incorporated by reference herein.

BACKGROUND

Technical Field

This disclosure relates to optical shape sensing instruments and more particularly to a lumen for use with shape sensing optical fibers which protects and permits rotation of the optical fibers.

Description of the Related Art

Optical shape sensing (OSS) uses light along a multicore optical fiber for device localization and navigation during surgical intervention. Shape sensing based on fiber optics exploits the inherent backscatter in a conventional optical fiber. The principle involved makes use of distributed strain measurement in the optical fiber using characteristic Rayleigh backscatter or controlled grating patterns.

Integrating an optical shape sensing fiber into a medical device can provide localization information for use during navigation inside the body. Many interventional devices have small cross-sectional footprints that limit the amount of space available for including an optical fiber. In addition, the manner in which the fiber is integrated into the device can affect both the performance of the OSS and the device.

Optical fiber used to perform a shape sensing measurement may be integrated into the medical device such that traditional performance of that device is unaltered. Limited space within a footprint of a device also makes it challenging to integrate the optical fiber. OSS may use a calculation of strain along a multi-core optical fiber to reconstruct the shape along the fiber. As such, the shape stability and reconstruction accuracy are susceptible to changes in tension, twist, vibration, and pinching. Integrating this technology into interventional devices used in a dynamic environment, such as that of vascular navigation, can cause significant degradation of OSS performance

SUMMARY

In accordance with the present principles, a shape sensing enabled instrument includes a flexible longitudinal body including a plurality of longitudinal members held together to form a lumen. The longitudinal members have frictional contact therebetween and are configured to engage neighboring longitudinal members during bending, twisting or external pressure to maintain dimensions of the lumen. A shape sensing optical fiber is disposed within the lumen.

A shape sensing system includes a shape sensing enabled medical instrument including a flexible longitudinal body having a plurality of longitudinal members held together to form a lumen. The longitudinal members have frictional contact longitudinally therebetween and are configured to engage neighboring longitudinal members during bending, twisting or external pressure to maintain dimensions of the lumen. At least one shape sensing optical fiber is disposed within the lumen. A console is configured to receive optical signals from the at least one shape sensing optical fiber and interpret the optical signals to determine a shape of the instrument.

A method for sensing a shape of a shape sensing enabled instrument includes providing a shape sensing enabled medical instrument including a flexible longitudinal body having a plurality of longitudinal members held together to form a lumen, the longitudinal members having frictional contact therebetween, the longitudinal members being configured to engage neighboring longitudinal members during bending, twisting or external pressure to maintain dimensions of the lumen; receiving optical signals from one or more optical fibers disposed in the lumen; and interpreting the optical signals to determine a shape of the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 2 is a perspective view showing a cross-section of a helical stranded hollow tube in accordance with one illustrative embodiment;

FIG. 3 shows cross-sectional views of exemplary single and dual (multi) layer stranded tubes in accordance with illustrative embodiments;

DETAILED DESCRIPTION OF EMBODIMENTS

Figure 1:
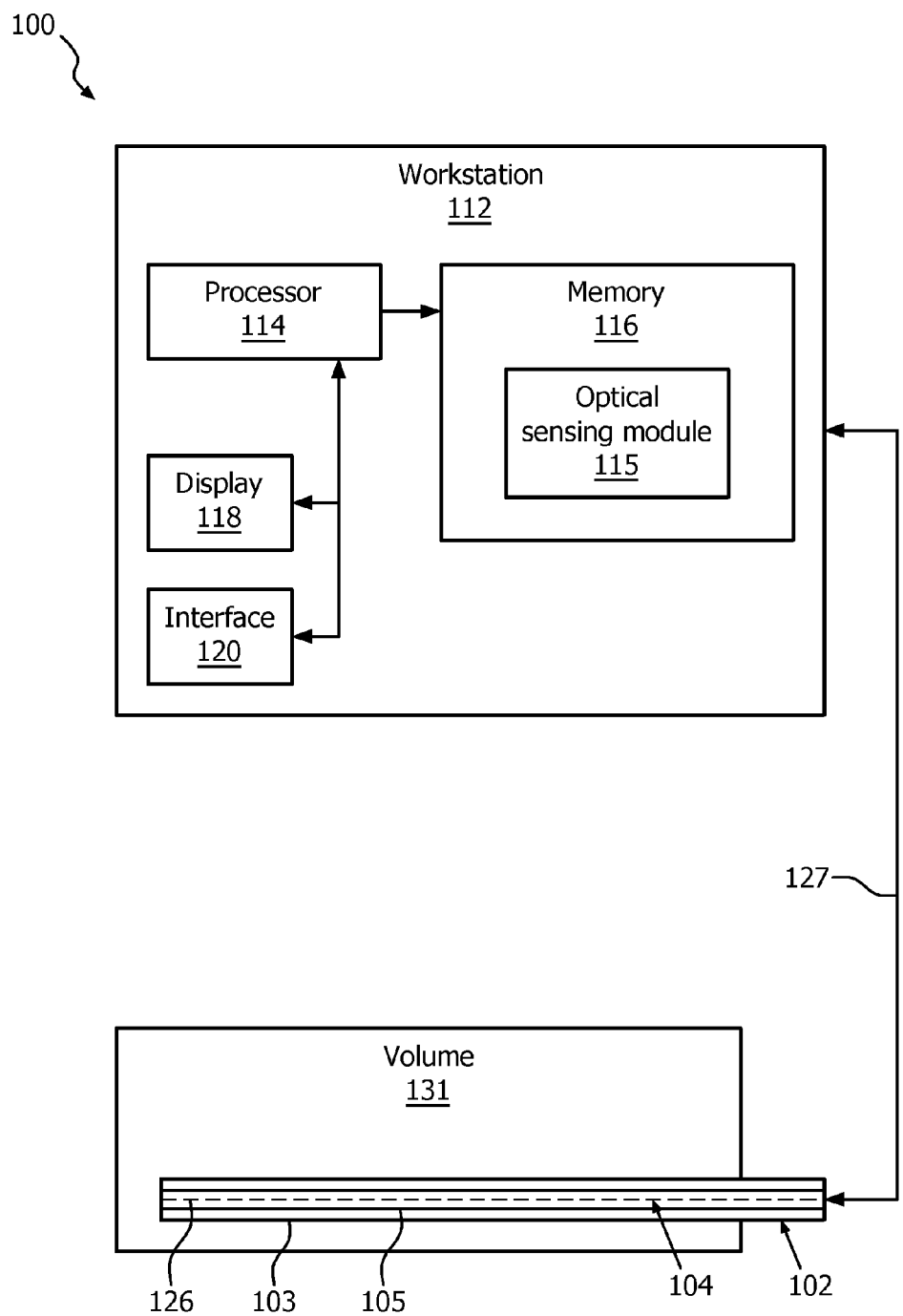
FIG. 1 is a block/flow diagram showing a shape sensing system which employs a stranded tube for receiving a fiber therein in accordance with one embodiment.

In accordance with the present principles, an optical fiber carrying lumen is configured to improve shape sensing performance by dampening vibrations from an external environment, providing a smooth, continuous and pinch-free lumen, and permitting the fiber to slide freely within the lumen. Shape sensing performance can also be improved by decoupling torque of the device from the twisting of the fiber.

In accordance with the present principles, a multi-purpose lumen design is employed for interventional devices that resolves at least three challenges in fiber integration. These include limited cross-sectional area available in the device, protection and isolation of the fiber from the external environment, and decoupling of external torquing from fiber twist.

The lumen houses the OSS fiber and restrains and controls the motion of the OSS fiber. The motion controlled may include, e.g., reduction in longitudinal stick-slip behavior (tension) due to friction between the shape sensing fiber and the lumen wall during curvature induced path length changes, reduction in rotational stick-slip due to friction between the fiber and the lumen wall during torquing of the device, bending of the device to accommodate an anatomy no longer resulting in ovalization of the lumen, reduction in vibration due to wall scraping of a tip of the device, clinician handling of the instrument, blood flow around the device, heart beat motion, etc. These effects may or may not occur independently, and frequently one effect can cause or compound another.

Further, there is a limited cross-sectional area available for the optical fiber in existing medical device designs. This means that it is desirable that the lumen within which the optical fiber is placed be as small as possible, while still providing a buffer for the fiber from the external environment.

In accordance with the present principles, a lumen design for the integration of an OSS fiber into an elongated medical device, includes, but is not limited to, one or more of the following. A reduction of stick-slip behavior is achieved through a textured, braided, multi-filar (single or multi-layer), or non-uniform inner surface of the lumen. A structured circular (braided) or non-circular lumen cross section (i.e., hexagonal) is provided with rotationally isotropic mechanical properties (i.e., no preferential mechanical bending direction), which can be composed of a coiled multi-filar tube, for reduction of lumen ovalization during bending. Vibration dampening is provided through a lumen composed of twisted filars, strands, or threads that has a low spring constant for absorption of high frequency vibrations, such as those found during manipulation of medical devices.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for using shape sensing enabled devices is illustratively shown in accordance with one embodiment. System 100 may include a workstation or console 112 from which a procedure is supervised and/or managed.

Workstation 112 preferably includes one or more processors 114 and memory 116 for storing programs and applications. Memory 116 may store an optical sensing module 115 configured to interpret optical feedback signals from a shape sensing sensor or system 104. Optical sensing module 115 is configured to use/interpret the optical signal feedback (and any other feedback, e.g., electromagnetic (EM) tracking) to reconstruct deformations, deflections and other changes associated with a medical device or optical shape sensing enabled device 102 and/or its surrounding region. The medical device 102 may include a catheter, a guidewire, a probe, an endoscope, a robot, an electrode, a filter device, a balloon device, or other medical component, etc.

An optical sensor 104 is placed inside of a suitable lumen for the fiber that will dampen vibration, provide structural support to prevent ovalization and pinching of the fiber, and can provide more room for the fiber. In some cases, the fiber can be rotationally isolated from external torquing through the multi-purpose design of the lumen.

The shape sensing enabled instrument 102 includes a flexible longitudinal body 103 including an outer surface which encapsulates interior features. The interior features include an optical fiber lumen 105 configured to receive one or more optical fibers for optical shapes sensing. The flexible longitudinal body 103 includes a textured, braided, multi-filar (single or multi-layer), or other non-uniform inner surface of the lumen 105. A structured circular (braided) or non-circular lumen cross section (e.g. hexagonal) with rotationally isotropic mechanical properties (i.e., no preferential mechanical bending direction) can be composed of a coiled multi-filar tube, for reduction of lumen ovalization during bending. Vibration dampening through the lumen 105 composed of twisted filars, strands, or threads preferably has a low spring constant for absorption of high frequency vibrations, such as those found, e.g., during manipulation of medical devices. Stick-slip behavior between the optical fiber sensor and the lumen 105 is reduced by using a low-friction fiber optic coating or coating/polishing surface in contact with the optical fiber coating.

In one embodiment, a passive electrically charged coating or passive magnetic coatings may be employed on both the lumen surface and the sensor surface in which like charge distributions or magnetic poles repel each other and minimize interactions between the two surfaces. Direct braiding or coiling of the fiber may be employed to reduce vibration and stick-slip behavior while also reducing the necessary lumen size.

For a given fiber sensor outer diameter and a given lumen structural configuration, a calibration process can be applied to compute an optimal ratio of lumen diameter to sensor diameter. The outcome of this calibration process provides a set of optimal geometric ratios for each sensor and lumen material type that will allow for the best trade-offs between minimizing overall device cross-sectional footprint and maximizing the available buffer space between sensor and lumen for mechanical isolation. For example, in a Pebax™ lumen a ratio of 2:1 between the lumen inner diameter and fiber outer diameter may be desired to achieve the same performance as a nitinol lumen with a ratio of 3:2.

A reduction of stick-slip behavior between the sensor and lumen is achieved by using a low friction coefficient between the fiber optic coating and the lumen material the fiber is in. A reduction of stick-slip behavior between sensor and lumen may also be achieved by using passive electrically charged coatings on both the lumen surface and the sensor surface in which like charge distributions repel each other and minimize interactions between the two surfaces (analogous to negatively-charged proteins on the blood vessel walls that repel the negatively-charged surfaces of red blood cells). In another embodiment, reduction of stick-slip behavior between sensor and lumen may be achieved by using passive magnetic coatings on each surface that lead to magnetic repulsion and friction minimization between the two components.

Direct braiding or coiling of the fiber may be also provided to reduce vibration and stick-slip behavior while also reducing the necessary lumen size. In one embodiment the lumen includes a hollow helical stranded with filars in a single or dual layer made of stainless steel (e.g., 304V stainless steel) with an outer diameter suitable for use as a guide wire and with an inner diameter to accommodate an optical shape sensing fiber 126.

With regard to decoupling of twist, the accuracy of the optical shape sensing position degrades with increased twist along the length of the sensor 104. Since torquing of medical instruments is common in many procedures, there is considerable value in designing devices to decouple or reduce the torquing of the device from the twisting of the fiber sensors. The present principles decouple the instrument torquing from the twisting of the fiber.

The shape sensing sensor 104 on device 102 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing sensor 104 with on fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

In one embodiment, workstation 112 receives feedback from the shape sensing sensor 104, and position data as to the location, position/rotation (shape) of the sensing sensor 104 is provided within a volume 131 (e.g., a patient). An image of the shape sensing sensor 104 within the space or volume 131 can be displayed on a display device 118. Workstation 112 includes the display 118 for viewing internal images of a subject (patient) or volume 131 and may include the image as an overlay or other rendering of the sensing sensor 104. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A lumen is provided in the devices that includes the optical fiber therein and reduces the negative effects of vibration, pinching, twisting and friction on the fiber and includes a lumen diameter to buffer the fiber from the external environment. A structured lumen cross-section for reduction of lumen ovalization during bending, vibration dampening effects and a continuous lumen with no transitions or pinch points is provided.

Referring to FIG. 2, a side view (SV) and a cross-sectional (CS) view of a helically stranded hollow tube 200 are shown in accordance with an illustrative embodiment. The tube 200 includes inner filars 202 and outer filars 204. The inner filars 202 are configured to form a lumen 205, which is configured to receive a shape sensing optical fiber or fibers (not shown) therein. The lumen 205 may have the shape of a circle, a polygon (e.g., a hexagon, as shown), or any other symmetrical shape. The filars 202 and 204 are helically wound about a central axis of the tube 200. The filars 202 and filars 204 may be counter wound (wound in opposite directions) with respect to one another or wound in a same direction on a different helical pitch. One or more of the filars 202 and filars 204 may be braided or woven through one another. The filars 202 and 204 are depicted to include a cross-sectional shape that includes a thicker center portion 220 than end portions 222 due to the cross-section cut through the helical wrap and to permit easier wrapping or coiling around the lumen 205.

The filars 204 may have an external coating or skin 224. The coating 224 may include a polymer, a thin metal foil or other material. The helical pitch may be controlled by the filar 202, 204 properties. The filar diameter and number of filars as well as the pitch of the filars controls the bending flexibility of the tube 200 as well as a spring constant and resulting vibration dampening.

The filars 202 and 204 are capable of developing gaps or spaces from their neighboring filars to permit flexibility for rotation and twist of the tube 200 during use. The filars 202 and 204 are configured to engage each other (e.g., frictional engagement) at the end portion under external pressure, twisting, bending, etc. to resist crushing of the lumen 205 by external forces or pressures.

Vibration dampening properties are achieved by the helically wound strand or strands. Stranding may be configured in a way to suppress high frequency vibrations (for example, greater than 100 Hz) that may occur during clinical manipulation of devices. The vibration suppression may be controlled by a number of filars, a size of the filars, a property of the material, etc. Different applications will have different vibration dampening needs, which can be selected by the properties of the stranded lumen 205. In one embodiment, scan time of the optical shape sensing system determines the sensitivity to vibration. Any motion or changes occurring during a sweep can corrupt that measurement data. Therefore, the vibration properties of the device should be optimized to the optical shape sensing parameters (specifically the sweep time of a laser source).

In one embodiment, the tube 200 includes six filars 202 in a first layer and six filars 204 in a second layer. In one example, each filar 202, 204 may include a thickness of about 0.006". The filars 202, 204 may be made of 304V stainless steel or other suitable material. The tube 205 may include an outer diameter of 0.032" (suitable for use as a guide wire) with an inner diameter of 0.020" to accommodate an optical shape sensing fiber. Other dimensions and sizes may be employed.

Referring to FIG. 3, a single layer stranded structure 210 and a multi-layered stranded structure 212 are depicted with a circular cross-section lumen 205. The structures 210 and 212 each form a hollow tube formed of strands 232 and/or 234 (which can be solid or hollow). The strands 232, 234 may be captured between an internal coating or tube 236 and an external coating or tube 238. The coatings 236 and 238 may include a thin walled sheath or tube that maintains the strands in their relative positions.

Figure 4:
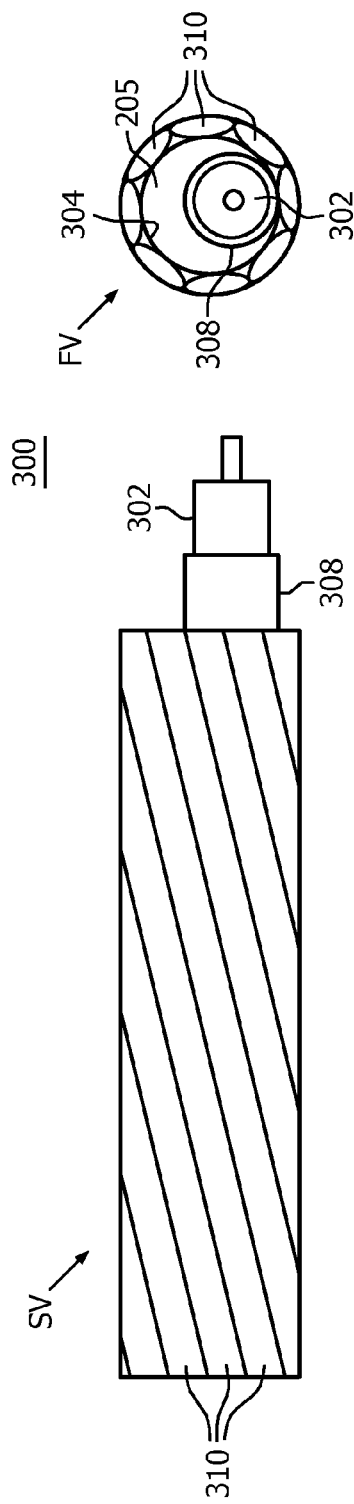
FIG. 4 is a perspective view showing a cross-section of a helical stranded hollow tube in accordance with one illustrative embodiment.

Referring to FIG. 4, a structure 300 (which may be similar to those depicted in FIGS. 2 and 3) is provided to control motion of optical fibers placed within the lumen 205. The structure 300 includes a side view (S) and a front view (FV). Longitudinal stick-slip behavior (tension) due to friction between a shape sensing fiber 302 and a lumen wall 304 during curvature induced path length changes is reduced. Rotational stick-slip due to friction between the fiber 302 and the lumen wall 304 during torquing of the device is also reduced. Bending of the structure 300 to accommodate the anatomy, resulting in possible ovalization of the lumen is reduced or avoided. Vibration (due to wall scraping of its tip, clinician handling, blood flow around the structure 300, heart beat motion, etc.) is reduced by the structure 300 due to the plurality of longitudinal members or strands 310, which provide a cage-like structure with gaps that significantly reduce stiffness of the entire assembly. These effects may or may not occur independently, and frequently one effect can cause or compound another. The lumen 205 within which the optical fiber 302 is placed is preferably as small as possible, while still providing a buffer for the fiber 302 from an external environment.

The structure 300 provides a lumen that has an optimal design for the integration of an OSS fiber into an elongated medical device, including, but not limited to a reduction of stick-slip behavior through a textured, braided, multi-filar (single or multi-layer), or non-uniform inner surface of the lumen. A structured circular (braided) or non-circular lumen cross section (e.g., hexagonal) with rotationally isotropic mechanical properties (i.e., no preferential mechanical bending direction) can be composed of a coiled multi-filar tube for reduction of lumen ovalization during bending. Vibration dampening is achieved through a lumen composed of twisted filars, strands, or threads that have a low spring constant for absorption of high frequency vibrations, such as those found during manipulation of medical devices. Vibration reduction is also achieved by material selection, coatings, stiffness, etc.

The vibration dampening property of the helically wound strands can be configured in a way to suppress high frequency vibrations (for example, >100 Hz) that may occur during clinical manipulation of devices. In useful embodiments, the vibration suppression is controlled by the number of filars, size of the filars, property of the material, etc. Different applications will have different vibration dampening needs, which can be selected by the properties of the stranded lumen. A scan time of the optical shape sensing system can determine sensitivity to vibration. Any motion or changes occurring during the sweep corrupt that measurement data. The vibration properties of the device may be optimized to the optical shape sensing parameters (specifically the sweep time of the laser source).

For a given fiber sensor outer diameter and a given lumen structural configuration, a calibration process may be applied to compute an optimal ratio of lumen diameter to sensor diameter. The outcome of this calibration process will be to provide a set of optimal geometric ratios for each sensor and lumen material type that will allow for the best trade-offs between minimizing overall device cross-sectional footprint and maximizing the available buffer space between sensor and lumen for mechanical isolation. Reduction of stick-slip behavior between sensor 302 and lumen wall 304 may be improved by providing a low-friction fiber optic coating 308. Other friction reduction techniques may include textured surfaces on the interior surface of the lumen 205, smooth lumen 205 surfaces, low friction coatings (lumen 205 and/or fiber coating 308), etc.

Figure 5:
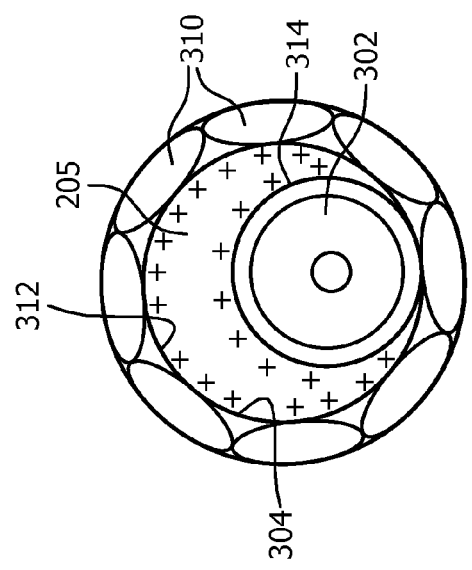
FIG. 5 is a cross-sectional view showing a stranded tube with an electrically charge on a lumen wall and a fiber coating to cause a repelling force therebetween in accordance with one illustrative embodiment.

Referring to FIG. 5, a reduction of stick-slip behavior between sensor 302 and lumen wall 304 may be enhanced by using passive electrically charged coatings 312 and 314 on both a lumen surface and a sensor surface in which like charge distributions repel each other and minimize interactions between the two surfaces. This in effect reduces interaction between the surfaces, and if interaction occurs, frictional forces are reduced due to reduced normal forces. Positive charge is illustratively depicted as "+" signs but negative charge may be employed as well. The charge may be provided using material coatings (e.g., polymers, magnetic paint, etc.), or by preparing the fiber and lumen with static charge prior to integration. Alternatively, the properties and/or coatings of the lumen and fiber can be chosen such that they remain neutral and do not accumulate static charge during interaction, so as to minimize any attractive force between the fiber and the lumen.

Figure 6:
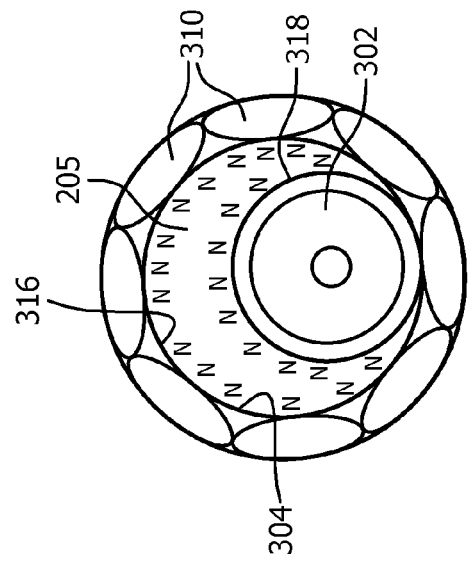
FIG. 6 is a cross-sectional view showing a stranded tube with magnetic features on a lumen wall and a fiber coating to cause a repelling force therebetween in accordance with one illustrative embodiment.

Referring to FIG. 6, a reduction of stick-slip behavior between sensor 302 and lumen wall 304 may be achieved by using passive magnetic coatings 316 and 318 on each surface that leads to magnetic repulsion and friction minimization between the two components. This in effect reduces interaction between the surfaces, and if interaction occurs, frictional forces are reduced due to reduced normal forces. A north pole is illustratively depicted as "N" but south poles may be employed as well. The magnetic materials may be integrated in thin coatings on the lumen and sensor surfaces that lead to mutual repulsion. Examples of such magnetic thin films include single-crystal, polycrystalline, amorphous, or multilayered atomic arrangements of ferro/ferrimagnetic transition-metal based alloys (e.g., iron, cobalt, other rare earths, etc.) which have magnetic moments that can be manipulated to control the degree of repulsion between interfaces. Active electromagnetic coatings can also be applied as an alternative to passive coatings to reduce friction forces between the lumen and sensor.

It should be understood that the present embodiments are not limited to a single sensing fiber. Multiple sensing fibers can be contained within a lumen of the structures described. The multiple sensing fibers can be used for sensing shape, strain, temperature, flow, etc. The present principles apply to any integration of optical shape sensing into medical devices including manual catheters, actuated catheters (both manual and robotic), guide wires, stylets, endoscopes and bronchoscopes, ultrasound probes, etc.

It should also be understood that while the present embodiments have been described using multiple strands, the number of strands may be as low as a single strand. A single stranded tube may be employed by coiling a single strand so that adjacent coils are in contact or may even have a gap between adjacent twists.

Figure 7:
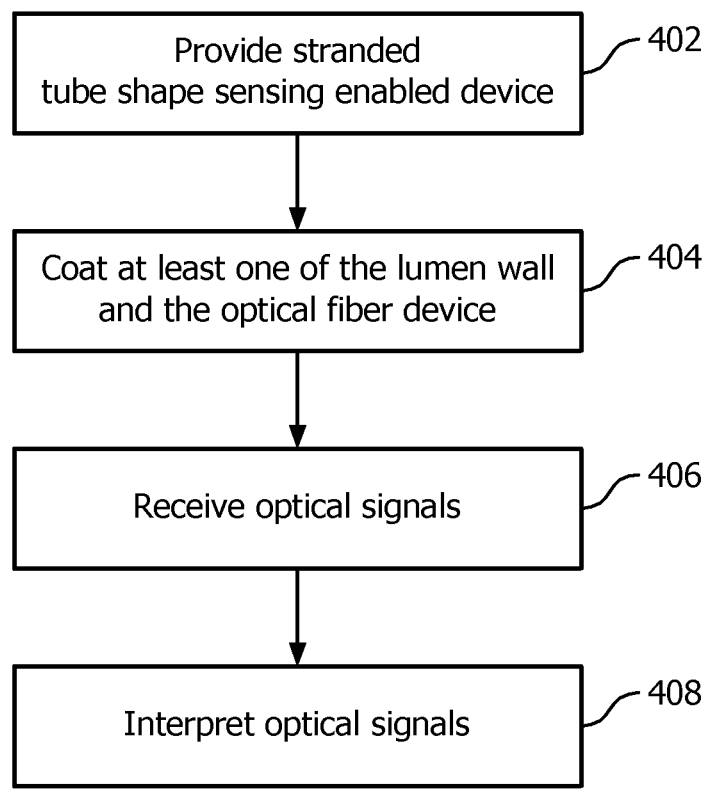
FIG. 7 is a block/flow diagram showing a method for sensing a shape of a shape sensing enabled instrument in accordance with illustrative embodiments.

Referring to FIG. 7, a method for sensing a shape in a shape sensing enabled instrument is shown in accordance with the present principles. In block 402, a shape sensing enabled medical instrument is provided including a flexible longitudinal body having a plurality of longitudinal members held together to form a lumen, the longitudinal members having frictional contact longitudinally therebetween, the longitudinal members being configured to engage neighboring longitudinal members during bending, twisting or external pressure to maintain dimensions of the lumen. In block 404, at least one of a lumen wall and the one or more optical fibers are coated to reduce friction therebetween. This may include using smooth or textured materials configured to reduce friction or the coating of the optical fiber and the lumen may repel each other using, e.g., a same electrical charge or a same magnetic polarity on each of the coating and the wall.

In block 406, optical signals are received from one or more optical fibers disposed in the lumen. In block 410, the optical signals are interpreted to determine a shape of the instrument.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for lumen design for optimal fiber integration for optical shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A shape sensing enabled instrument, comprising:
a flexible longitudinal body comprising a plurality of adjacent, helically wrapped, longitudinally-extending members, extending in parallel to each other, the longitudinally-extending members being held together and have a frictional contact therebetween, wherein the longitudinally-extending members provide a lumen in space surrounded by interior faces of the plurality of longitudinally-extending members;
the longitudinally-extending members being configured to engage neighboring longitudinally-extending members during bending, twisting or external pressure to maintain dimensions of the lumen; and
at least one shape sensing optical fiber disposed within the lumen and surrounded by the interior faces of the plurality of longitudinally-extending members, wherein: at least a wall of the lumen includes a same electrical charge as a coating on the at least one shape sensing optical fiber to repel the at least one shape sensing optical fiber; or at least a wall of the lumen includes a same magnetic polarity as a coating on the at least one shape sensing optical fiber to repel the at least one shape sensing optical fiber.

2. The shape sensing enabled instrument as recited in claim 1, wherein the plurality of adjacent, helically wrapped, longitudinally-extending members have a configuration that is sufficient to suppress vibrations that occur during manipulation of the instrument.

3. The shape sensing enabled instrument as recited in claim 1, wherein the plurality of adjacent, helically wrapped, longitudinally-extending members includes at least one of filars and strands.

4. The shape sensing enabled instrument as recited in claim 1, wherein the plurality of adjacent, helically wrapped, longitudinally-extending members includes one or more helically wrapped strands about a longitudinal center axis.

5. The shape sensing enabled instrument as recited in claim 1, wherein the lumen is a round lumen, or a polygonal lumen.

6. The shape sensing enabled instrument as recited in claim 1, wherein the lumen includes a coating configured to reduce friction with the at least one shape sensing optical fiber.

7. The shape sensing enabled instrument as recited in claim 1, wherein the coating on the at least one shape sensing optical fiber is configured to reduce friction with the lumen wall.

8. The shape sensing enabled instrument as recited in claim 1, wherein the plurality of adjacent, helically wrapped, longitudinally-extending members includes multiple layers of at least one of filars and strands.

9. A shape sensing system, comprising:
a shape sensing enabled medical instrument including a flexible longitudinal body having a plurality of adjacent, helically wrapped, longitudinally-extending members, extending in parallel to each other, the longitudinally-extending members being held together and have frictional contact therebetween, wherein the longitudinally-extending members form a lumen in space surrounded by interior faces of the plurality of longitudinally-extending members, the longitudinally-extending members being configured to engage neighboring longitudinally-extending members during bending, twisting or external pressure to maintain dimensions of the lumen;
at least one shape sensing optical fiber disposed within the lumen and surrounded by the interior faces of the plurality of longitudinally-extending members wherein: at least a wall of the lumen includes a same electrical charge as a coating on the at least one shape sensing optical fiber to repel the at least one shape sensing optical fiber; or at least a wall of the lumen includes a same magnetic polarity as a coating on the at least one shape sensing optical fiber to repel the at least one shape sensing optical fiber; and
a console configured to receive optical signals from the at least one shape sensing optical fiber and interpret the optical signals to determine a shape of the shape sensing enabled medical instrument.

10. The shape sensing system as recited in claim 9, wherein the coating on the at least one shape sensing optical fiber is configured to reduce friction with the lumen wall.

11. The shape sensing system as recited in claim 9, wherein the plurality of adjacent, helically wrapped, longitudinally-extending members have a configuration that is sufficient to suppress vibrations that occur during manipulation of the shape sensing enabled medical instrument.

12. The shape sensing system as recited in claim 9, wherein the plurality of adjacent, helically wrapped, longitudinally-extending members includes at least one of filars and strands.

13. The shape sensing system as recited in claim 9, wherein the plurality of adjacent, helically wrapped, longitudinally-extending members includes one or more helically wrapped strands about a longitudinal center axis.

14. The shape sensing system as recited in claim 9, wherein the lumen includes a coating configured to reduce friction with the at least one shape sensing optical fiber.

15. A method for sensing a shape of a shape sensing enabled instrument, comprising:
providing a shape sensing enabled medical instrument including a flexible longitudinal body having a plurality of adjacent, helically wrapped, longitudinally-extending members, extending in parallel to each other, that are held together and have frictional contact therebetween, wherein the longitudinally-extending members form a lumen in space surrounded by interior faces of the plurality of longitudinally-extending members, the longitudinally-extending members being configured to engage neighboring longitudinally-extending members during bending, twisting or external pressure to maintain dimensions of the lumen;
receiving optical signals from one or more shape sensing optical fibers disposed in the lumen, said shape sensing optical fibers being surrounded by the interior faces of the plurality of longitudinally-extending members wherein: at least a wall of the lumen includes a same electrical charge as a coating on at least one shape sensing optical fiber of the one or more shape sensing optical fibers to repel the at least one shape sensing optical fiber; or at least a wall of the lumen includes a same magnetic polarity as a coating on the at least one shape sensing optical fiber to repel the at least one shape sensing optical fiber; and
interpreting the optical signals to determine a shape of the instrument.

16. The method as recited in claim 15, wherein the coating on the at least one shape sensing optical fiber is configured to reduce friction with a lumen wall.

* * * * *